US 6,636,581 B2

(12) United States Patent
Sorenson (10) Patent No.: US 6,636,581 B2
(45) Date of Patent: Oct. 21, 2003

(54) INSPECTION SYSTEM AND METHOD

(76) Inventor: Michael R. Sorenson, 1625 Peachey Rd., Ashland, OR (US) 97520

( * ) Notice: Subject to any disclaimer, the term of this patent is extended or adjusted under 35 U.S.C. 154(b) by 199 days.

(21) Appl. No.: 09/944,693

(22) Filed: Aug. 31, 2001

(65) Prior Publication Data

US 2003/0043964 A1 Mar. 6, 2003

(51) Int. Cl.$^7$ .............................................. G01N 23/02
(52) U.S. Cl. ..................................................... 378/58
(58) Field of Search .............................. 378/57, 58, 62, 378/70–81, 20; 356/237, 237.3, 237.4; 250/201.3, 201.6, 559, 48, 358.1

(56) References Cited

U.S. PATENT DOCUMENTS

| 3,678,736 | A |   | 7/1972  | May .............................. 73/67.8 |
|-----------|---|---|---------|-------------------------------------------|
| 3,949,229 | A |   | 4/1976  | Albert .......................... 250/401  |
| 4,057,745 | A |   | 11/1977 | Albert .......................... 313/55   |
| 4,170,145 | A |   | 10/1979 | Kennedy et al. ............... 73/620      |
| 4,803,639 | A | * | 2/1989  | Steele et al. ................... 702/40   |
| 4,907,157 | A |   | 3/1990  | Uyama et al. ........... 364/413.13        |
| 5,014,293 | A |   | 5/1991  | Boyd et al. .................. 378/197     |
| 5,112,131 | A |   | 5/1992  | Pryor .......................... 356/376   |
| 5,124,554 | A | * | 6/1992  | Fowler et al. ............ 250/358.1       |
| 5,237,598 | A |   | 8/1993  | Albert .......................... 378/99   |
| 5,318,254 | A |   | 6/1994  | Shaw et al. .................. 244/134     |
| 5,490,646 | A |   | 2/1996  | Shaw et al. .................. 244/134     |
| 5,524,038 | A |   | 6/1996  | Fong .............................. 378/4   |
| 5,754,617 | A | * | 5/1998  | Itoh ............................... 378/4  |
| 5,917,590 | A | * | 6/1999  | Greve ....................... 356/237.3    |
| 5,930,330 | A |   | 7/1999  | Wolfe et al. ................. 378/98.2    |
| 6,064,717 | A |   | 5/2000  | Ortega et al. .................. 378/71    |
| 6,154,522 | A |   | 11/2000 | Cumings ..................... 378/206      |
| 6,192,759 | B1 |  | 2/2001  | Schoess ........................ 73/583    |
| 6,220,099 | B1 |  | 4/2001  | Marti et al. ................... 73/633    |

* cited by examiner

Primary Examiner—William Oen
(74) Attorney, Agent, or Firm—White & Case LLP (57) ABSTRACT

An inspection system utilized to inspect a structure for particularities, including defects, includes a first gantry with a detector inspection device that is placed in a known position on one side of the structure, and a second gantry with a source inspection device that is placed on the other side of the structure. In an embodiment, the detector inspection device is an x-ray detector inspection device and the source inspection device is an x-ray source inspection device. The movement of the first and second gantries is controlled by a gantry control system. A data acquisition system controls the data, e.g., image, collection process. During the data collection process, the relative positions of the source and detector inspection devices are initialized. The detector and source inspection devices are then moved in synchronized motion to each data collection position, such that the relative alignment of the inspection devices is maintained. In an embodiment, a programmed inspection sequence directs data collection positioning for automated coverage of the structure. In an alternative embodiment, manual positioning may be utilized. The detector and source inspection devices collect data, e.g., images, of the structure at each data collection position.

56 Claims, 4 Drawing Sheets

INSPECTION SYSTEM AND METHOD

FIELD OF THE INVENTION

This invention relates generally to inspection methods for identifying structural particularities and, more particularly, to an inspection method for identifying defects, including cracks and corrosion, in aircraft.

BACKGROUND

"Aging aircraft" is a Federal Aviation Administration (FAA) classification for a commercial aircraft with over 36,000 cycles on its airframe, or 15 years of service life, or a combination of cycles and years of service life. A cycle comprises a takeoff and landing. Worldwide, there are thousands of aircraft in the "aging aircraft" category.

The FAA requires that an aging aircraft be inspected for cracks and corrosion at regular intervals. Current known inspection techniques use visual inspection. To prepare for a visual inspection, the interior of the fuselage must be stripped of seats, bins, galleys, panels, and insulation. Further, the visual inspection process itself typically takes several personnel ten days or more to complete. Moreover, it has been found that a crack may not be identified with a visual inspection until it reaches a length of two to four inches. Additionally, cracks and corrosion on the interior layers or frame members cannot be seen at all using visual inspection. Overall, the visual inspection technique is slow, laborious, damaging to aircraft materials, and less than optimally effective for crack and corrosion detection.

Alternative non-invasive inspection techniques, such as x-ray inspection, would provide superior detection of cracks and corrosion in an aircraft fuselage. Additionally, the aircraft's panels and insulation would not have to be removed. However, there is currently no practical way of performing a comprehensive x-ray inspection of an aircraft. To obtain an x-ray image through a fuselage (or wing) requires that an x-ray source or emitter and an x-ray detector, located inside and outside of the fuselage respectively, be positioned with respect to each other at the time that the images are obtained.

Accordingly, those skilled in the art have long recognized the need for a new method of efficiently performing an inspection of an aircraft. The present invention clearly fulfills these and other needs by providing the means to perform an efficient and non-invasive inspection, reducing the time and cost required to prepare an aircraft for inspection, reducing the time to perform the inspection, and increasing the effectiveness and quality of the inspection. The structure and method of the present invention may also be used to identify components, or particularities, of any structure, including, for example, ships and buildings.

SUMMARY

Briefly, and in general terms, the present invention resolves the above and other problems by providing an inspection method for inspecting a structure and identifying particularities, such as defects, in the structure. The inspection method includes: positioning two inspection devices at a pre-determined distance from each other, one of the inspection devices inside of the structure and the other inspection device outside of the structure, wherein the two inspection devices comprise a detector inspection device and a source inspection device; collecting data, such as images, of a portion of the structure located between the source and the detector; moving the inspection devices on the inside and the outside of subsequent portions of the structure to be inspected while maintaining an approximate distance between the inspection devices without reliance on a physical or optical link between the inspection devices; and collecting data of the additional portions of the structure located between the inspection devices.

In accordance with an aspect of the present invention, the inspection devices are automatically moved to each portion of the structure to be inspected according to an inspection sequence that controls the movement of the inspection devices along the structure. In an embodiment, the inspection sequence is a programmed inspection sequence. The programmed inspection sequence that controls movement of the inspection devices along the structure may be produced at some time prior to the inspection by an operator moving one or both of the inspection devices through data collection positions and programming the data collection positions into the inspection sequence. In an embodiment, during the creation of the programmed inspection sequence, sections of the inspection sequence that correspond to similar or substantially similar portions of the structure are repeated within the inspection sequence during the programming, thereby, among other things, simplifying the programming of the inspection sequence.

In an embodiment, the programmed inspection sequence that controls movement of the inspection devices along the structure is produced from surface data generated from visual surveying equipment. In another embodiment, the programmed inspection sequence is produced from surface model data derived from Computer Assisted Design (CAD) data. In yet another embodiment, the source inspection device and the detector inspection device are manually moved to each portion of the structure to be inspected.

In accordance with another aspect of the present invention, the source inspection device comprises an x-ray source and the detector inspection device comprises an x-ray detector. In an embodiment, the source is mounted on a first gantry and the detector is mounted on a second gantry. A gantry is a motion control device that allows positioning of an inspection device at a desired position. A gantry consists of two or more linked mechanical structures, the relative positions of which are controlled by actuators. A construction crane or a "cherry picker" are examples of gantries. The first and second gantries are synchronized to move in coordinated motion with each other under the direction of a gantry control system. Alternatively, it is not required that both gantries move in strict synchronization; it is only required that the inspection devices stop at prescribed relative positions so that satisfactory data, such as images, can be acquired. Either of these types of relative motions will be referred to herein as synchronized motion.

In another embodiment, one inspection device is mounted on an interior gantry that utilizes a track assembly and the other inspection device is mounted on an exterior gantry that utilizes a rover vehicle. A rover vehicle is a ground-based vehicle that carries the external gantry from point to point. In an embodiment, the rover has four-wheel independent steering to increase maneuverability.

In accordance with another aspect of the present invention, the inspection devices are initialized at home positions that allow for direct or visual contact between the inspection devices. In an embodiment, the task of initializing a gantry or inspection device consists of moving the inspection device to a known location and entering into the motion control system the coordinates of the known location either in the gantry or the coordinate system of the structure to be inspected, e.g., the aircraft coordinate system. In another embodiment, the task of initializing a gantry or inspection device consists of moving the gantry to a known internal configuration, or home position, and entering into the motion control system the gantry coordinate system values for that position. In yet another embodiment, the task of initializing a gantry or inspection device consists of moving two inspection devices to specific locations relative to each other and entering into the motion control system the relative coordinates of one or both inspection devices or gantries.

In an embodiment, the structure that the inspection method is designed to inspect comprises an aircraft. Additionally, in an embodiment the particularities that the inspection method identifies comprise cracks and corrosion. In an alternative embodiment, the structure that the inspection method is used to inspect comprises any structure, including, but not limited to, a building or a ship.

Another embodiment of the present invention is also directed towards an inspection method for identifying particularities, such as defects, in a structure. The inspection method includes: placing a first gantry having an attached inspection device in a known position located outside of the structure; placing a second gantry having an attached inspection device inside of the structure, wherein the inspection devices comprise a detector inspection device and a source inspection device; initializing the relative positions of the inspection devices; moving the inspection devices in a coordinated manner to each data, e.g., image, collection position according to an inspection sequence that controls movement of the inspection devices along the structure while maintaining the relative alignment of the inspection devices; and collecting data, e.g., images, of the structure at each data collection position.

In accordance with an aspect of the present invention, the motion of a gantry can be mathematically derived from the desired motion of the respective inspection device, where the desired motion of the inspection device is characterized with respect to an inspection device based coordinate system. The coordinate axis system of the inspection device is defined as a set of artificial axes. The term artificial is used to denote the fact that the inspection device's coordinate axes typically have no one corresponding gantry motion directly associated with them. Generally, to move an inspection device along one of its artificial axes typically requires that two or more gantry axes be actuated.

In an embodiment, the artificial axes are correlated, or otherwise registered, to the geometry of the structure to be inspected, e.g., the aircraft geometry. The artificial axes allow an operator to move the inspection device in its coordinate system, thereby simplifying the operator's task of maintaining the inspection device in a constant orientation relative to the surface of the structure to be inspected, e.g., parallel or perpendicular to the aircraft fuselage, at all times as the inspection device is moved along the structure. Without the use of the artificial axes of the inspection device, the operator would be required to characterize the desired motion of the inspection device with respect to the gantry axes, and manually manipulate several gantry axes at the same time while simultaneously attempting to follow the changing geometry of the structure to be inspected, e.g., the aircraft.

In an embodiment, once the position of one of the inspection devices is determined, a corresponding position for the second inspection device is obtained. The position of the second inspection device can be an offset from the first inspection device position. In an embodiment, the offset is the distance between the inspection devices along an artificial axis, such as the normal axis to the first inspection device's front surface. The required motion of the gantry supporting the second inspection device to move the second inspection device to a designated position can be mathematically derived by a process of reverse kinematics.

Reverse kinematics utilizes the gantry geometry, the location and orientation of the inspection device on the gantry, and the desired position of the inspection device to adjust the gantry actuators appropriately. In an embodiment, reverse kinematics can be utilized to generate a set of motions for a second gantry that will achieve a sequence of data collection positions for the second inspection device corresponding to a programmed sequence of data collection positions for the first inspection device. In an embodiment, reverse kinematics may be utilized to derive a set of interior gantry motions that will achieve a sequence of image collection positions for an x-ray source inspection device corresponding to a programmed sequence of image collection positions for an x-ray detector inspection device, while maintaining the relative alignment and synchronized motion of the inspection devices. In an alternative embodiment, reverse kinematics can be utilized to derive a single position at a time for the second, e.g., source or interior, inspection device, and then repeated to retain synchronization of the second inspection device with the first, e.g., detector or exterior, inspection device for each new position of the first inspection device.

In an embodiment, the data collection, such as imaging, of each portion of the structure under inspection is performed when the motions of the gantries are intermittently stopped.

Another embodiment of the present invention is a method for creating an inspection sequence to be used in inspecting a structure for particularities, such as defects. This method includes: aligning an exterior gantry having an inspection device with the structure to be inspected; initializing all axes of the exterior gantry; creating at least three reference points at known locations on the structure; determining the location and orientation of the inspection device relative to the structure via triangulation to the reference points; determining data, e.g., image, collection positions for the inspection device of the exterior gantry; positioning and orienting the attached inspection device with respect to the structure at the data collection positions and recording the data collection positions; and, using reverse kinematics to derive a set of interior gantry motions that will achieve a sequence of data collection positions for the inspection device on the interior gantry corresponding to a programmed sequence of image collection positions for the inspection device on the exterior gantry, while maintaining the relative alignment and synchronized motion of the inspection devices.

In accordance with an aspect of the present invention, the inspection sequence is programmed to automatically move the inspection devices to each data, e.g., image, collection position on the structure. In an embodiment, the inspection device of the exterior gantry comprises an x-ray detector and the inspection device of the interior gantry comprises an x-ray source. In an embodiment, the exterior gantry is a master system and the interior gantry is a slave system.

Another embodiment of the present invention is an inspection method for identifying particularities, such as defects, in a structure. The inspection method includes: locating an exterior rover gantry having a detector inspection device to a pre-determined home position outside the structure and correlating, or registering, the gantry to the structure; mounting an interior rail gantry having an x-ray source inspection device onto alignment tracks at a predetermined home position located inside the structure; aligning the detector inspection device of the exterior gantry with the x-ray source inspection device of the interior gantry through physical or optical or other applicable means; implementing an inspection sequence to move the detector inspection device and the source inspection device to each image collection position; and obtaining an x-ray image at each image collection position with the inspection devices. In an embodiment, the inspection sequence is a programmed inspection sequence for automatically moving the detector and source inspection devices to each image collection position. In an embodiment, the inspection method can utilize an alignment system for referencing the structure, including, but not limited to a target alignment system, a laser alignment system, a radio frequency alignment system, a physical alignment systems, or an optical alignment system. Other known alignment techniques may also be utilized.

Another embodiment of the present invention is an inspection system for identifying particularities, such as defects, in a structure. The inspection system includes a coordinated dual gantry system, a source inspection device, a detector inspection device and a gantry control system. The coordinated dual gantry system includes an exterior gantry that is configured to move externally to the structure and an interior gantry that is configured to move internally to the structure in synchronized motion with the exterior gantry. One of the inspection devices is mounted on the exterior gantry and the other inspection device is mounted on the interior gantry. The gantry control system maneuvers the detector inspection device and the source inspection device in synchronized motion with each other to each data, e.g., image, collection position on the structure, according to a programmed inspection sequence that controls movement of the inspection devices along the structure. In an embodiment, the gantry control system maneuvers the detector and source inspection devices while maintaining the relative alignment of the detector and the source at each data collection position. Together the inspection devices collect data, such as an image, from each data collection position on the structure.

In accordance with an aspect of the present invention, the inspection system includes an image acquisition system that controls image collection. In another embodiment, the inspection system includes a sensor or sensors which can accurately determine the location of the detector inspection device with respect to the structure just before data collection takes place. In an embodiment, the inspection system utilizes an alignment system such as, but not limited to, a target alignment system, a laser alignment system, a radio frequency alignment system, a physical alignment system, or an optical alignment system. In an embodiment, the exterior gantry is a master system and the interior gantry is a slave system.

In an embodiment, artificial axes are utilized that allow an operator to move an inspection device in a coordinate system that continually updates in space with respect to the orientation of the inspection device, rather than requiring desired motion of the inspection device to be input with respect to gantry axes. In an embodiment, the artificial axes register to, or are otherwise correlated with, the coordinate system of the structure to be inspected, e.g., the aircraft coordinate system. In an embodiment, reverse kinematics are utilized to derive a set of interior gantry motions that will achieve a sequence of data collection positions for the source inspection device corresponding to a programmed sequence of data collection positions for the detector inspection device, while maintaining the relative alignment and synchronized motion of the inspection devices.

Other features and advantages of the present invention will become apparent from the following detailed description, taken in conjunction with the accompanying drawings, which illustrate by way of example, the features of the present invention.

DETAILED DESCRIPTION OF THE DRAWINGS

In the following description, for purposes of explanation, numerous specific details are set forth in order to provide a thorough understanding of the present invention. It will be apparent, however, to one skilled in the art, that the present invention may be practiced without these specific details. In other instances, well-known structures, devices and methods are shown in block diagram form and/or described more generally, in order to avoid unnecessarily obscuring the present invention.

An embodiment inspection system and method, constructed in accordance with the present invention, provides an efficient inspection system and technique for locating and identifying particularities, such as defects, in a structure. In an embodiment system and methodology of the present invention, the structure being inspected is an aircraft (e.g., fuselage and/or wings). In other embodiments the inspection system and method are used to examine other structures, including by way of example only, and not by way of limitation, fuel tanks and other pressure vessels. An embodiment inspection system and method reduces the time and cost required to prepare a structure, such as an aircraft, for inspection when compared to current visual inspection techniques. An embodiment inspection system and method also reduces the time to perform an inspection and increases the effectiveness and quality of the inspection.

Although the method and system of inspection may be used with a variety of structures to be inspected, for ease of discussion herein, the method and system will be described with respect to the inspection of an aircraft. Additionally, although the method and system of the present invention is not limited to use of x-ray inspection via image collection at various inspection points, and can encompass other inspection methods via, more generally, data collection at various inspection points, for ease of discussion, the method and system will be described herein with respect to x-ray inspection.

Figure 1:
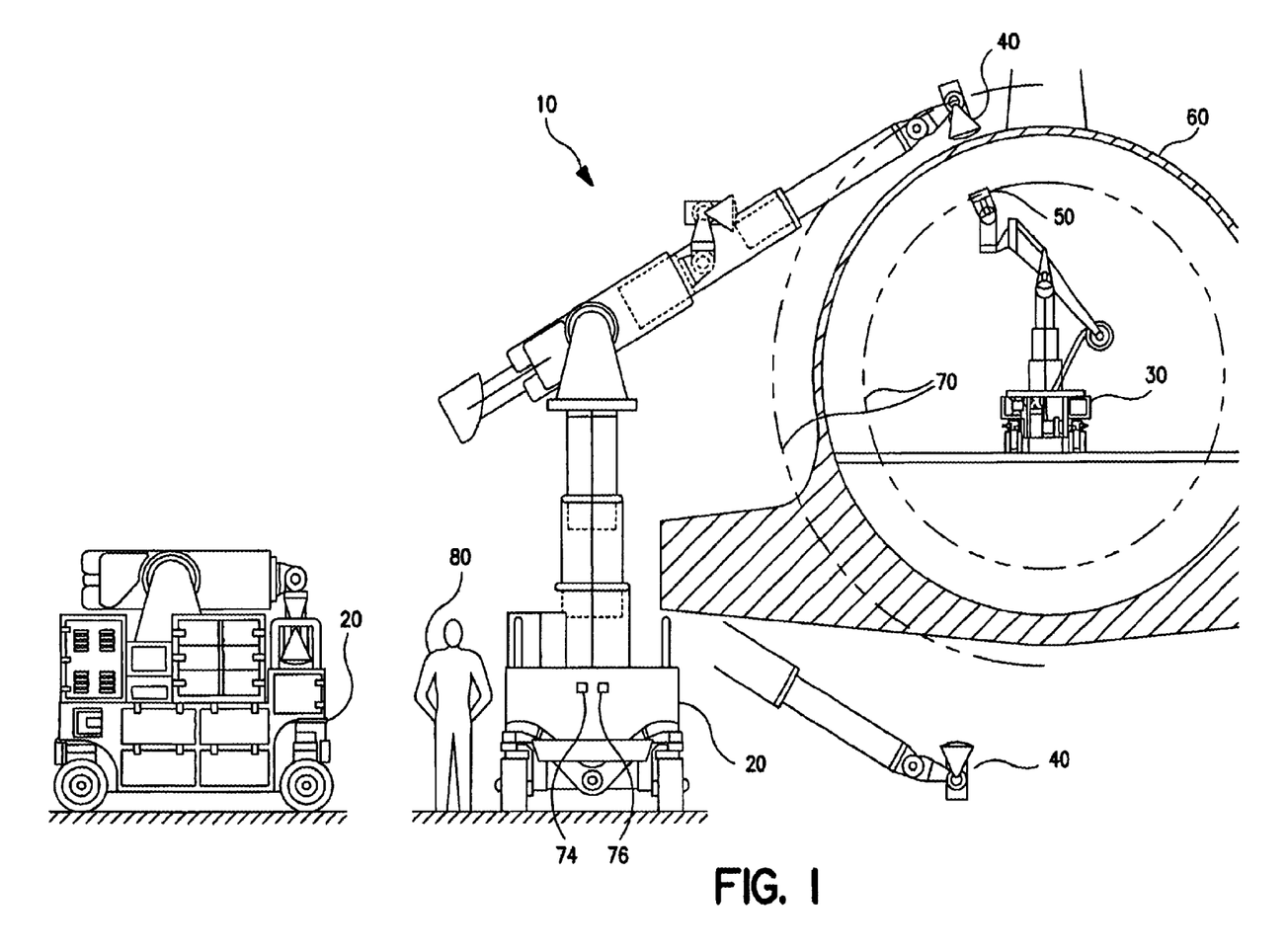
FIG. 1 illustrates a perspective view of an embodiment of an inspection system for inspecting an aircraft fuselage.

Referring now to the drawings, wherein like reference numerals denote like or corresponding parts throughout the drawings and, more particularly to FIG. 1, there is shown an embodiment inspection system 10. In an embodiment, the inspection system 10 of the present invention is utilized to inspect aging aircraft for defects, including by way of example only, and not by way of limitation, cracks and corrosion. In this embodiment, a first gantry 20 with an x-ray detector inspection device 40 is placed in a known position located outside of the aircraft fuselage 60, and a second gantry 30 with an x-ray source inspection device 50 is placed inside of the aircraft fuselage 60. The relative positions of the detector inspection device 40 and source inspection device 50 are then initialized. The detector inspection device 40 and source inspection device 50 are moved in a coordinated manner to each image collection position, such that the relative alignment of the detector inspection device 40 and source inspection device 50 is maintained.

In an embodiment, a programmed inspection sequence 70 directs image collection positioning for automated coverage of the fuselage 60. In an alternative embodiment, manual positioning is utilized. In an embodiment system 10 of the present invention, the detector inspection device 40 is placed on the exterior gantry 20, and the source inspection device 50 is placed on the interior gantry 30 for improved image quality. In an alternative embodiment, a reverse arrangement of the location of the x-ray source inspection device 50 and x-ray detector inspection device 40 is utilized. In alternative embodiments, non-destructive inspection techniques other than x-rays are used, such as ultrasound, thermography, and eddy current.

An x-ray inspection system 10, in accordance with the present invention, provides many desirable functions. Specifically, the inspection system 10 is capable of rapidly and accurately positioning an x-ray source inspection device 50 and a detector inspection device 40 in and around an aircraft (or other structure) to be inspected. The inspection system 10 is capable of rapid assembly and disassembly, as well as registering the system's position with respect to the aircraft. The inspection system 10 is capable of executing an inspection sequence 70 with respect to the aircraft and exporting aircraft-based coordinates during the process. Further, the inspection system 10 produces, on command, smooth motions of the source inspection device 50 and the detector inspection device 40 to prescribed positions, such that the source inspection device 50 and the detector inspection device 40 are coaxial along the source beam at a known distance during the image capture process. In an embodiment, the inspection system 10 includes software and tools for creating and reviewing motion programs. In an embodiment, the inspection system 10 of the present invention includes standard computer interfaces for communication control and status reporting, as well as safety provisions for preventing injury to personnel or damage to the structure under examination.

Inspection System Components

An embodiment inspection system 10 of the present invention utilizes several different pieces of equipment, including an exterior gantry 20, an interior gantry 30, an x-ray detector inspection device 40 and an x-ray source inspection device 50. Additionally, position sensing equipment, alignment instruments and support equipment (e.g., electronics, power supply, and cabling), which are known in the art, are also utilized as needed. An embodiment of the x-ray inspection system 10 includes two independent, self-propelled gantry systems (the exterior gantry 20 and the interior gantry 30) which are controlled by a common gantry control system 74. In an embodiment, the exterior gantry 20 is a boom-type system, which houses the x-ray detector inspection device 40, and utilizes ground-based "rover" technology, as well as self-leveling jacks. In an embodiment, the interior gantry 30 is a track-based, boom-type system, which houses the x-ray source inspection device 50, and utilizes a conventional track system for longitudinal movement.

In an embodiment, the gantry control system 74 is contained in the exterior gantry 20, or is otherwise associated with the exterior gantry 20, and provides input and feedback capabilities for the operator 80, as well as a communication interface for exterior control, data sharing, and handshaking. An embodiment of the present invention further includes an image acquisition system 76 that coordinates image collection. In an embodiment, the image acquisition system 76 fully automates the image collection process once the x-ray inspection system components have been installed and aligned, and the inspection sequence 70 has been programmed (or reloaded from non-volatile memory storage) for controlling the movement of the inspection devices along the structure to be inspected. Further, the image acquisition system 76 may also record detector inspection device 40 and source inspection device 50 position data, as well as the corresponding image data produced by the detector inspection device 40 and source inspection device 50.

In an embodiment, the exterior gantry 20 consists of a mechanism with eight independent axes of motion (track-x, track-y, boom azimuth, boom elevation, boom telescopic, head pan, head tilt, and head roll). In an embodiment inspection system, all axes of motion, except for head roll, are motorized and computer controlled. In an embodiment, a motorized vehicle, e.g., a rover, transports the exterior gantry 20 and includes locking features to fix the exterior gantry 20 firmly to the ground. This vehicle also provides a ninth axis of motion to the exterior gantry 20 along the axis of the fuselage 60 (z-axis).

In another aspect, a digital x-ray detector inspection device 40 is mounted to the end of the exterior gantry 20. In an embodiment, the x-ray detector inspection device 40 consists of a panel. In an alternative embodiment, the x-ray detector inspection device 40 consists of discrete detectors. Position-sensing equipment, such as interferometers, laser range finders, cameras, optical targets, or other surveying and/or aligning equipment may also be utilized as needed. An embodiment also includes support electronics, a computer, and a user input interface. In an embodiment, correlation, or registration, of the exterior gantry 20 to an airframe, or other structure to be inspected, is accomplished using self-leveling jacks, active electronics, and procedural registration techniques known in the art.

Referring to another component of the present invention, the interior gantry 30 consists of a mechanism with typically five independent axes of motion (track Z, boom azimuth, boom elevation, head pan, and head tilt). An x-ray source inspection device 50, such as a scanning or a conventional fixed source (depending on the x-ray system used), is mounted to the end of the interior gantry 30. In an embodiment, alignment instruments or targets are also utilized as required. Other support equipment, such as associated electronics, power supplies, and cabling are also implemented as required.

In an embodiment inspection system 10 of the present invention, registration of the interior gantry 30 to the airframe (or other structure being inspected) is accomplished through accurate engagement between the gantry tracks and the aircraft cabin seating tracks, combined with procedural registration techniques known in the art. In an embodiment, set up and calibration is designed to be simple, well-defined, and repeatable.

Artificial Axes

In accordance with the inspection system 10 of the present invention, each gantry is capable of movement along several independent axes. Generally, however, the operator 80 is interested primarily in the motion of the detector inspection device 40 (or the source inspection device 50) at the end of the gantry 20, and not the motion of the gantry 20 itself. The axes of motion in an inspection device based coordinate system, which is defined as the set of artificial axes, are mathematically related to the axes of motion of the gantries 20 and 30. Since the geometry of the gantry 20 and gantry 30 are well characterized, the gantry control system 74 can derive the associated motion of the gantry axes from the desired motion of the inspection device that an operator 80 inputs into a gantry user interface. The inspection device based coordinate system is designated herein as artificial axes. An embodiment gantry user interface allows an operator 80 to command and control the gantries 20 and 30, and the inspection devices 40 and 50. An embodiment gantry user interface includes a screen capable of displaying a graphical user interface ("GUI") and one or more user input devices, such as a keyboard, spaceball, mouse, trackball, etc.

In an embodiment, use of the artificial axes allows an operator 80 to move an inspection device in its coordinate system, thereby simplifying the operator's task of maintaining the inspection device in a constant orientation relative to the surface of the structure to be inspected, e.g., parallel or perpendicular to an aircraft fuselage, at all times as the inspection device is moved along the structure. Without artificial axes, the operator 80 would be required to characterize the desired motion of the inspection device with respect to gantry axes and manually manipulate several gantry axes at the same time while simultaneously attempting to follow the changing geometry of the structure to be inspected.

In addition, the artificial axes of the detector inspection device 40 can be registered to the control axes of a user input device, such as a spaceball. Then, if the operator 80 wants to move the inspection device 40 in a direction normal towards the surface of the structure to be inspected, a simple input is entered, e.g., pressing down on the spaceball. The gantry control system 74 software translates the simple artificial axes input, e.g., normal towards the surface of the structure, into a significantly more complicated and less intuitive motion along several combined gantry axes. Since the artificial axes follow the inspection device 40, i.e., the artificial axes are not fixed in space, the user's input is always intuitive.

The mathematics and data required for the artificial axes transformation are dependent only on the gantry and inspection device geometry, and do not require any inherent relationship to the object being inspected. However, the artificial axes can be explicitly aligned to the coordinate system of the structure to be inspected if so desired, as in the example above.

Inspection Method

Figure 2:
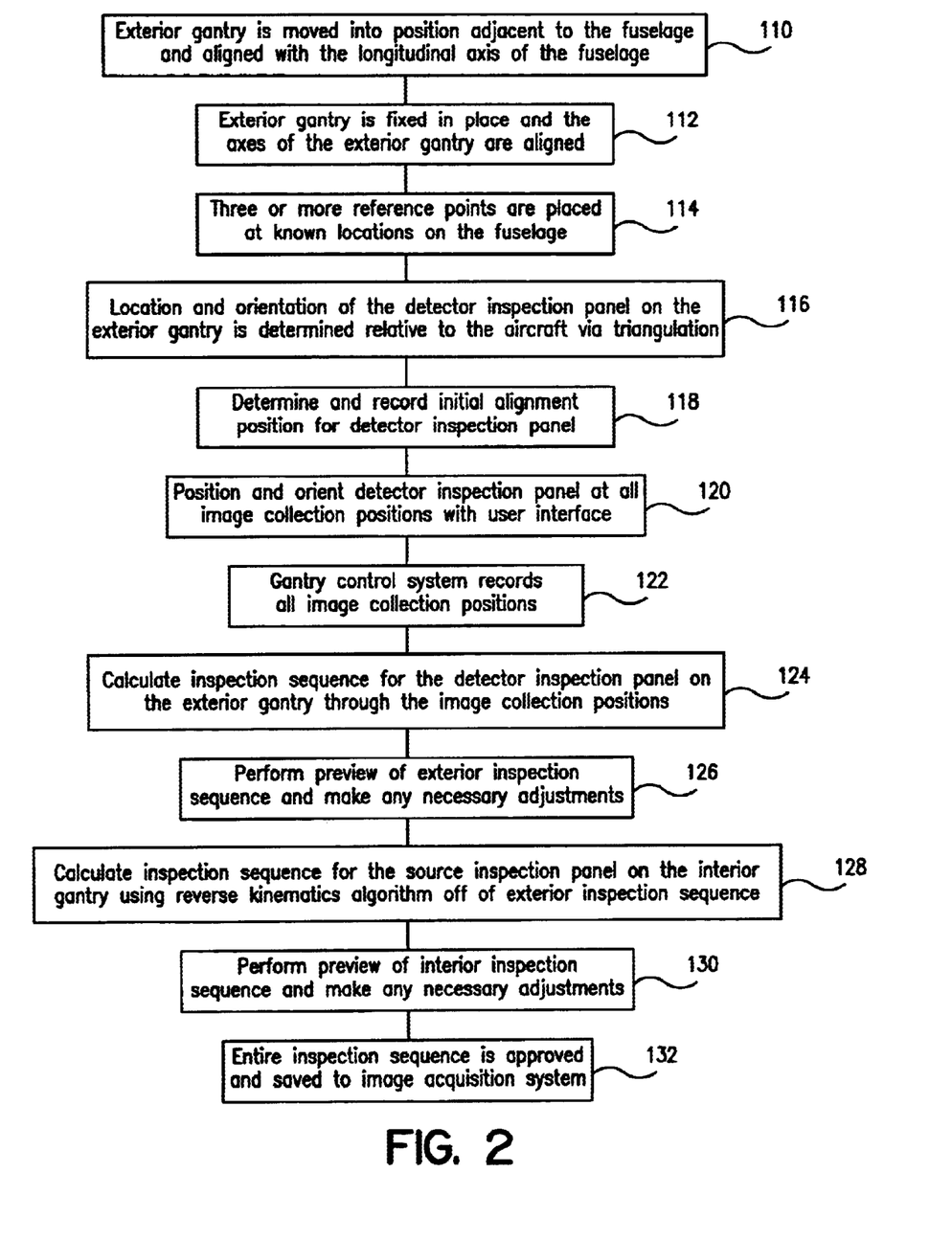
FIG. 2 illustrates an operational flow diagram of an embodiment of an inspection sequence for inspecting a structure.
Figure 3:
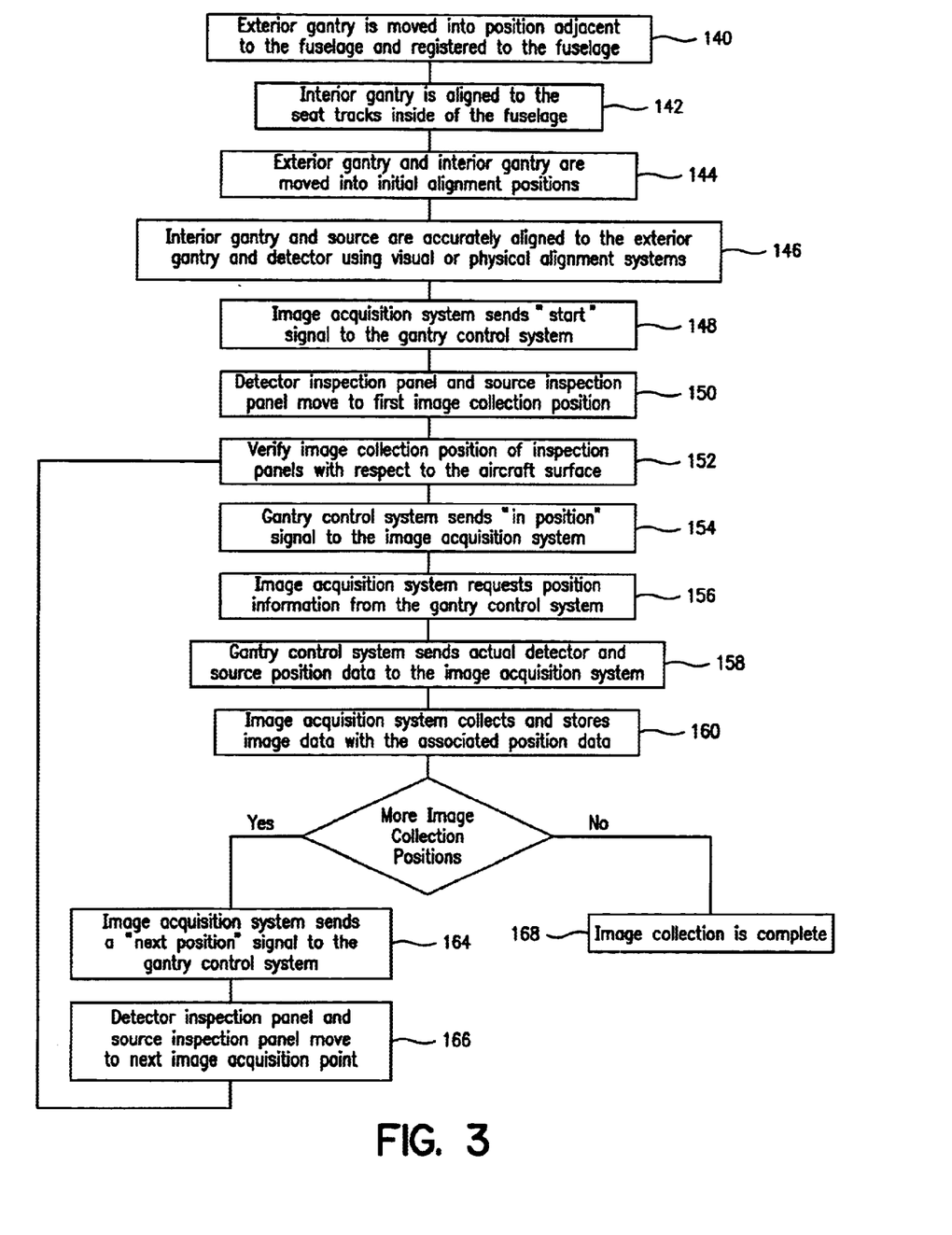
FIG. 3 illustrates an operational flow diagram of an implementation of an inspection sequence for inspecting a structure.

Referring now to FIG. 2, one portion of an embodiment inspection method of the present invention is the programming of an inspection sequence 70. The inspection process can be accomplished either by automatically (as shown in FIG. 3) or by manually moving the detector inspection device 40 and source inspection device 50 to each desired data, e.g., image, collection position on the aircraft (or other structure to be inspected). Manual inspection sequencing does have some drawbacks. For example, there are a large number of identical aircraft that can be inspected in an identical manner, yet manual inspection sequencing cannot generally take advantage of this type of aircraft similarity. Additionally, large sections of an aircraft are very similar in configuration and can be inspected in an identical, or substantially similar, manner, yet manual inspection sequencing cannot generally take advantage of this type of repetition.

Further, an operator 80 must be fairly precise in moving the inspection devices 40 and 50 to the inspection positions on an aircraft. Since there can be on the order of three thousand different inspection positions on an aircraft, the manual process tends to be extremely slow and tedious. The extra time involved with manual inspection sequencing is a significant cost burden to the service that performs the inspection (or to the airline itself). Moreover, an operator 80 must take numerous precautions in order to be protected from the scattered x-ray radiation. Therefore, it is generally undesirable for an operator 80 to have to be involved in tedious manual alignment of the inspection devices, while still having to maintain the necessary x-ray radiation precautions. For these and other reasons, it is advantageous to implement an automated inspection method in accordance with the present invention. However, in some embodiments of the present invention, manual inspection sequencing may still be utilized, for instance, if the geometry of the structure is unusual or difficult to program, if the motion control system has not been programmed with the geometry of the structure, for testing purposes, and so on.

As shown in FIG. 2, the first task in the automated process is to program the inspection sequence 70 into the gantry control system 74 for scanning the aircraft or other structure to be inspected. In an embodiment, this operation of programming the inspection sequence 70 is performed prior to any x-ray inspection. The inspection sequence 70 is created initially using only the exterior gantry 20 and some device simulating the geometry of the detector inspection device, which shall be called here the simulated detector. The detector inspection device 40 itself is not needed for this task, nor is the interior gantry 30. As described herein, "programming" refers to the process of defining a set of data points that constitute an inspection sequence 70 to be executed during image collection. The programming of the inspection sequence 70 of the present invention is usually only performed once per type of structure to be inspected, since subsequent structures of the same configuration can be inspected using the saved inspection sequence data.

This type of programming is a multi-step process consisting of several stages. The following describes an embodiment method of programming the inspection sequence 70 of the exterior gantry 20, as shown in FIG. 2. In preparation for the programming of the inspection sequence 70, the exterior gantry 20 (which is a rover in this embodiment), is moved adjacent to the aircraft of the type to be inspected. As described in Step 110, the rover 20 is positioned so that it is aligned with the longitudinal access of the aircraft. In an embodiment, the rover 20 is fixed in place with jacks. In Step 112, the axes of the rover 20 are initialized via interior home signals, limit switches, or the like. In Step 114 three or more reference points are then placed, or otherwise identified, on known fuselage 60 locations. In Step 116, the location and orientation of the simulated detector relative to the aircraft is then determined via triangulation to the reference points, using the surveying equipment located on, or otherwise associated with, the rover 20. In an embodiment, the surveying equipment is permanently mounted to the rover 20 in a known location.

Thereafter, the programming of the inspection sequence 70 for the exterior gantry 20 is commenced. In an embodiment, this process is assisted by the use of the artificial axes, as described above. The operator 80 uses the artificial axes to move the simulated detector in its coordinate system, thereby simplifying the operator's task of maintaining the simulated detector in an appropriate orientation, for instance normal to the aircraft, at all times as the simulated detector is moved along the aircraft. In Step 118 the operator 80 determines the position of an appropriate inspection sequence home location for the simulated detector. The home location for the simulated detector 40 is usually at an opening in the fuselage 60 through which the source inspection device and the detector inspection device can communicate, through physical or visual contact. This home location position is then recorded in an image acquisition system 76 in Step 118.

In Step 120, the simulated detector located on the exterior gantry 20 is then moved to desired image collection positions outside the airframe (or other structure to be inspected), where the simulated detector is then oriented. In an embodiment, the simulated detector is positioned with a user interface device that allows the operator 80 to control the input with up to six degrees of freedom.

Optionally, the operator 80 may specify the type of scan point(s) for the desired image collection points, e.g., web, lap joint, framers, or the like. Through techniques such as visual inspection, or use of programmed instructions to analyze schematics or other relevant structural design information, the position of the desired scan points can then be determined.

In an alternative embodiment, the operator 80 can move the simulated detector continuously without stopping while the image acquisition system continuously collects structure surface data from sensors mounted to the exterior gantry. Another embodiment employs operator 80 input parameters of known airframe characteristics. Through manual determinations, or more automated processes, the position of the image collection points can then be determined.

In Step 122, the gantry control system 74 records these image collection positions.

In Step 124, the inspection sequence 70 for the detector inspection device 40 on the exterior gantry 20 is calculated through the image collection positions that were recorded. In an embodiment, this is an automated process that can, if desired, interpolate a new set of image collection positions from the geometry derived from the original set of image collection positions.

Previewing of the exterior portion of the inspection sequence 70 is then performed in Step 126, and any necessary adjustments can be made. This process proceeds relatively quickly because the inspection method does not require stopping at each image acquisition position during previewing. This inspection sequence 70 for the exterior gantry 20 positions can subsequently be used again in its entirety, or with modifications, on all x-ray inspections of aircraft of similar type.

In an embodiment inspection method of the present invention, the efficiency of the inspection sequence 70 programming process for the exterior gantry 20 can be increased by using the following techniques. Specifically, many sections of the inspection sequence 70, which represent portions of the fuselage 60, can be copied to other sections of the inspection sequence 70, which represent other similar portions of the fuselage 60. For example, the inspection sequence 70 for one entire half of the fuselage 60, e.g., cut down the longitudinal access, can be mirrored for the other half of the fuselage 60. Also, since a fuselage is composed of geometrically similar arcs, the inspection sequence 70 data for an arc can be utilized at several sites along the fuselage 60. Further, the programming method does not require actual image locations to be recorded. Instead, the operator 80 can record a set of locations from which a generalized surface geometry of the aircraft can be deduced. The actual image collection locations can be interpolated using that geometry.

Another aspect of the inspection sequence 70 programming process, shown in Step 128, is the calculation of an inspection sequence 70 for the x-ray source inspection device 50 that is attached to the interior gantry 30. In an embodiment, this is an automated process referred to as "reverse kinematics" that, based on the inspection sequence 70 for the detector inspection device 40 and exterior gantry 20, generates a set of interior gantry motions that provides a synchronized inspection sequence 70 for the source inspection device 50 and interior gantry 30. In an embodiment inspection method of the present invention this process is implemented in the following manner. An offset is applied to determine the position of the source inspection device 50 relative to the detector inspection device 40 at each image collection position in the inspection sequence 70. An offset is a predefined distance between the source inspection device 50 and detector inspection device 40, which accounts for the thickness of the fuselage 60 or other intervening structure(s). Then, reverse kinematics is utilized to create the interior gantry 30 motions required to move the source inspection device 50 to its desired positions.

In an alternate embodiment inspection method of the present invention, other techniques for generating an inspection sequence 70 are utilized. In an embodiment, the aircraft surfaces are recorded using three-dimensional, visual-surveying instrument, e.g., optical or laser based. The inspection sequence 70 is then generated using this surface data. In other embodiments, blue prints or CAD data are used to generate a surface model of an aircraft from which an inspection sequence 70 is generated.

In another aspect of an embodiment inspection method, as shown in Step 130 of FIG. 2, the interior portion of the inspection sequence 70 is previewed and adjustments are made as necessary. During this procedure, both the detector inspection device 40 (or simulated detector) with attached exterior gantry 20, and the source inspection device 50 (or simulated source) with attached interior gantry 30, move through the inspection sequence 70 synchronously and smoothly. The process proceeds relatively quickly since the inspection sequence 70 does not need to stop at each image acquisition point during this procedure. In an embodiment, during the actual image collection inspection sequence 70, the detector inspection device 40 and source inspection device 50 stop at each image collection position for an x-ray image to be acquired, before moving on to the next image collection position, in a stop motion type of format. Additionally, arbitrary image acquisition points are selectable during test inspection sequences.

In Step 132 the inspection sequence 70 is approved and saved to the image acquisition system 76.

Referring now to FIG. 3, the next stage of the inspection method of the present invention involves the actual performance of the x-ray inspection. Initially, in Step 140 of this process, the exterior gantry 20 (e.g., rover) is moved into a position adjacent to the fuselage 60 and registered to, or otherwise aligned and/or coordinated with, the fuselage 60. In Step 142 the interior gantry 30 is assembled and aligned to the seat tracks located inside of the fuselage 60. Next, in Step 144 both gantries move into their pre-defined home positions. In an embodiment, in Step 146, the interior gantry 30 and source inspection device 50 are accurately aligned to the exterior gantry 20 and detector inspection device 40 using visual systems, including by way of example only, and not by way of limitation, collimation, triangulation, or other optical alignment techniques. In another embodiment, physical alignment techniques are utilized, where the inner gantry 30 contacts a registration alignment point on the exterior gantry 20 in order to initialize alignment of the detector inspection device 40 and the source inspection device 50. In another embodiment, the interior gantry 30 can visually or physically be aligned to points or targets with known locations on the interior of the aircraft.

Before image acquisition commences, the operator 80 moves to a remote location where the operator 80 is protected from the x-rays.

In an embodiment, during image acquisition, a typical sequence of events proceeds in the following manner. As shown in Step 148 of FIG. 3, the image acquisition system 76 signals the gantry control system 74 to start the cycle. In Step 150 the detector inspection device 40 with attached exterior gantry 20 and the source inspection device 50 with attached interior gantry 30 move to the first image acquisition point. In an embodiment, in Step 152 the exterior gantry 20 extends a detector touch ring to make contact with the aircraft surface, to verify the image collection position of the inspection panel with respect to the aircraft surface. In an alternative embodiment, other sensors can determine the normal, i.e., perpendicular, distance from the detector inspection device 40 to the structure. Next in Step 154, the gantry control system 74 signals the image acquisition system 76 that it is in position. In response, in Step 156, the image acquisition system 76 requests position information from the gantry control system 74. In Step 158, the gantry control system 74 then sends actual position data of the detector inspection device 40 and the source inspection device 50 to the image acquisition system 76. As shown in Step 160, the image acquisition system 76 then collects and stores image data with the associated position data. As long as there are additional image collection positions, in Step 164 the image acquisition system 76 signals the gantry control system 74 that it is ready for the next position.

When the inspection sequence 70 is complete, the gantry control system 74 signals the image acquisition system 76 that the cycle is complete, and returns to a ready condition. However, if the inspection sequence 70 is not complete but there is a required pause in the sequence (e.g., the exterior gantry 20 has to move to the other side of the aircraft wing), the gantry control system 74 signals the image acquisition system 76 to wait. Once repositioned and aligned, the gantry control system 74 signals the image acquisition system 76 to resume. The detector inspection device 40 and exterior gantry 20 and the source inspection device 50 and interior gantry 30 then move to the next image acquisition point in Step 166. This process is repeated until there are no additional image collection positions and, in Step 168, image collection is complete.

In an embodiment, the exterior gantry 20 and interior gantry 30 are limited in motion along the longitudinal axis (z-axis) of the aircraft. In this embodiment, the exterior gantry 20 and interior gantry 30 are indexed in the direction of the z-axis in discrete intervals, e.g., every 12–15 feet. In other embodiments of the present invention, the gantries have either no limitations in motion or different degrees of limitations in motion along the longitudinal axis of the aircraft. In an embodiment, after the gantries are moved to new locations, they are recalibrated to previously surveyed points so that alignment is maintained.

In another embodiment, a digital x-ray image is obtained at each image collection position. These images are exported and examined in real time by the operator 80 at a remote position, or, alternatively, the images can be stored for later review.

In an alternative embodiment, both a first gantry, for a detector inspection device 40, and a second gantry, for a source inspection device 50, are located outside the structure to be inspected, such as an aircraft, for inspecting components of the structure, including, for example, the aircraft wing. In an example of this alternative embodiment, both the first gantry and the second gantry are located outside of an aircraft, in relative positions to allow the detector inspection device 40 and source inspection device 50 to be advantageously aligned along data collection points on the aircraft wing. In this alternative embodiment, both the first gantry and the second gantry may utilize ground-based rover technology.

Exemplary System Features

The performance requirements of both the exterior gantry 20 and the interior gantry 30 are such that relatively low power actuators may be used. In an embodiment stepper motors are used as the actuators. Even without collision detection capability, the use of these actuators minimizes the risk of damage due to interference from a fixed object, because the actuator, by its nature or by design, will stall. Conversely, a typical servomotor will apply full power when encountering an obstacle. In an embodiment, an inspection system 10 of the present invention includes intelligent fault sensing and response for each axis of motion, to ensure that loss of signal will result in smooth gantry stops. An embodiment also uses absolute encoder feedback on all axes, which provides absolute axis position information in the event of a stall, power outage, or other problem.

In one exemplary embodiment of the present invention, the system components of the inspection system 10 include the following non-limiting characteristics. The exterior gantry 20 incorporates a rover consisting of a four-wheel ground vehicle onto which a telescopic column mounts. The rover unit employs a four-wheel drive, four-wheel steering approach for ground maneuvering. In an embodiment, two of the wheels (for instance the front wheels) are mounted to a pivoting beam which aids in ground handling. Further, an onboard battery, which is intended for removing the rover from its shipping container or trailer, is also capable of providing backup power to the system for a short time. An automated jack leveling and stabilizing system is also used in the inspection sequence 70 process. The rover also includes hard rubber, or urethane, wheels. In an embodiment, the central processing unit of the gantry control system 74, the user input device, and any other input devices, are located and stored on the rover.

In an embodiment, the telescopic column of the exterior gantry 20 is a multi-staged, electrically-driven column that is used to position the boom to the proper working height. An adjustable counterbalance cylinder carries the full load, so that the drive motor does not have to bear the fill weight of the column. Further, a hydraulic fail-safe valve locks the counterbalance cylinder in the event of a power loss, preventing the column from descending. In an embodiment inspection system 10 constructed in accordance with the present invention, a trunion and swing drive reside atop the column and manipulate the telescopic boom arm in azimuth and elevation. Stepper motors drive these axes, and utilize wear compensation. Advantageously, the trunion and drive swing are easily removable from the column via hoisting.

In another embodiment aspect of the inspection system 10, the boom arm is a multi-stage, telescopic apparatus with a mechanically linked dynamic counterbalance. Additionally, the exterior gantry 20 provides the movement of pan, tilt and portrait, as well as landscape (roll) manipulation to the detector inspection device 40. In an embodiment, the detector gantry also includes a touch ring and actuator or other position-sensing detectors.

The interior gantry 30 of an embodiment inspection system 10 houses the x-ray source inspection device 50 and includes a track with a double rail design that is lightweight and easily assembled. In an embodiment, the track lays flat on the cabin floor of the interior of the aircraft and disperses load evenly to meet aircraft loading requirements. In an embodiment, the track uses a rack system for linear drive engagement. In an alternative embodiment, the interior gantry 30 uses, although not necessarily includes, a track system.

The interior gantry 30 further includes a trunion with a swing drive that resides atop the column and manipulates the boom arm in azimuth and elevation. In an embodiment, both axes are driven by stepper motors which include wear compensation. Further, the trunion and swing drive are configured to be easily removable from the column. The boom arm of the interior gantry 30 is a simple fixed length structure with a mass counterbalance. The boom arm provides pan and tilt manipulation for the source inspection device 50, as well as providing a source collision sensor.

Alternative, One Inspection Device, Embodiments

Figure 4:
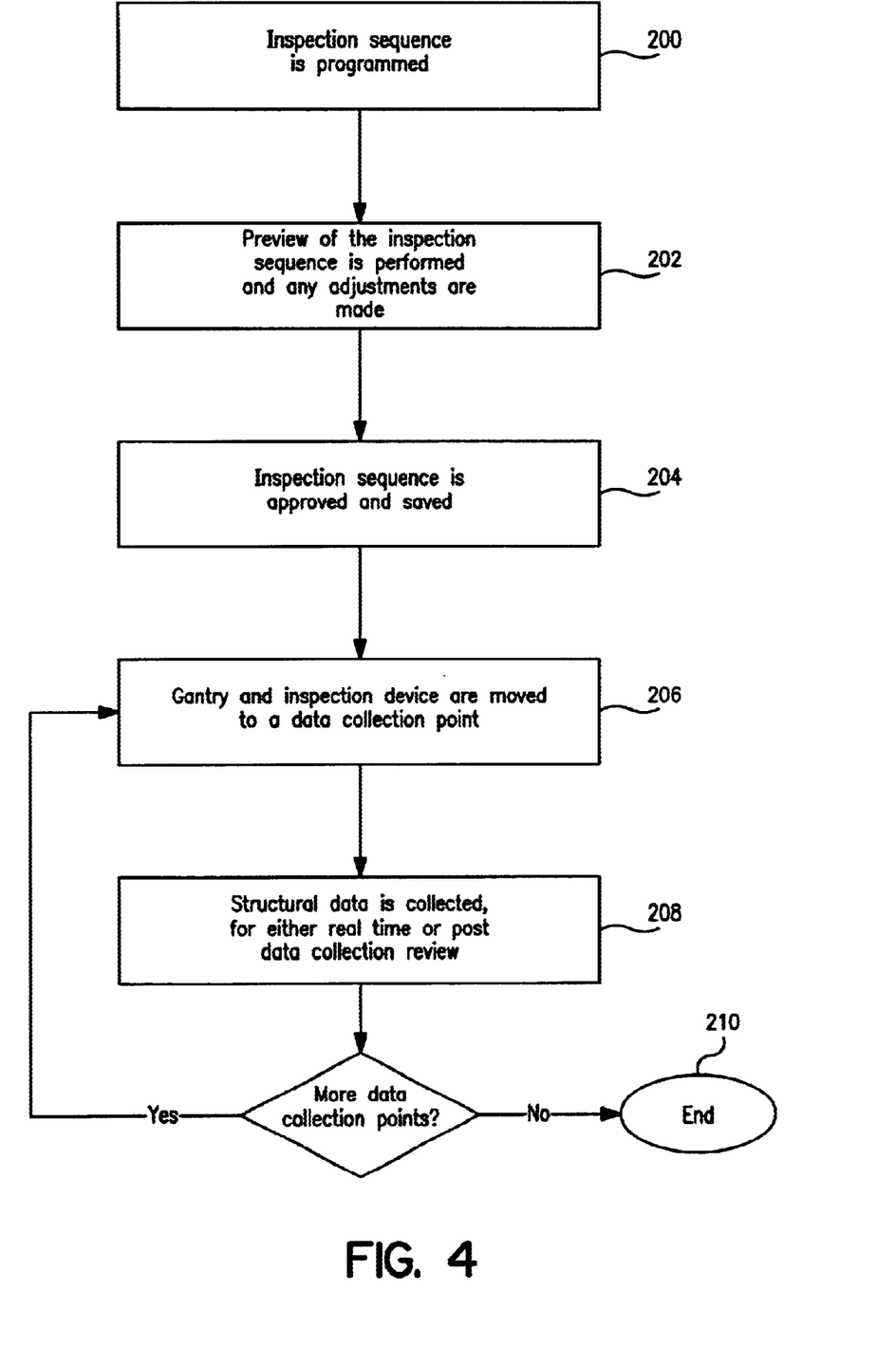
FIG. 4 illustrates an operational flow diagram of another embodiment of an inspection sequence for inspecting a structure.

In an alternative embodiment, one inspection device, positioned either internally, externally, or internally and then externally, or vice versa, is used to collect data from various data collection points on the structure to be inspected. As with other embodiments, as shown in FIG. 4, with a one inspection device embodiment, the inspection sequence is first programmed into the gantry control system in Step 200. In an embodiment, programming can be accomplished by moving a gantry that will hold the inspection device and a simulated inspection device adjacent to the structure to be inspected first to a home position, and then to each desired data collection position. Alternatively, the programming can be accomplished by using schematics or other relevant structural data for the structure to be inspected, and selecting a pattern to be used for inspection, e.g., every six inch block comprising the structural surface, or specific data collection points, or specific features of the structure to be inspected, e.g., lap joints, framers, etc. An inspection sequence is then calculated via the data collection points that were recorded, or otherwise determined.

In an embodiment, in Step 202 a preview of the inspection sequence can then be performed, and any adjustments to the sequence can be made. The inspection sequence is thereafter approved and saved in Step 204. The actual inspection performance can then be made, with the gantry and inspection device moving to each data collection point, in Step 206, and, in Step 208, collecting structural data for either real-time, or post data collection, review. This process is repeated until, in Step 210, there are no more data collection points. The review can be made either by an operator, or by an automated process using pre-defined criteria for reviewing the actual inspection data against.

The various system embodiments and methodologies described above are provided by way of illustration only and should not be construed to limit the invention. Those skilled in the art will readily recognize various modifications and changes may be made to the present invention without departing from the true spirit and scope of the present invention. Accordingly, it is not intended that the invention be limited, except as by the appended claims.

What is claimed is:

1. An inspection method for identifying particularities of a structure, the method comprising:

positioning a first inspection device inside of the structure and positioning a second inspection device outside of the structure, wherein one of the first or second inspection devices comprises a detector inspection device and the other of the first or second inspection devices comprises a source inspection device;

collecting data of at least a portion of the structure located between the first and second inspection devices;

moving the first inspection device on the inside and the second inspection device on the outside of a subsequent portion of the structure while approximately maintaining a pre-determined distance between the inspection devices; and collecting data at the subsequent portion of the structure located between the inspection devices.

2. The inspection method of claim 1, wherein the first and second inspection devices are automatically moved to the subsequent portion of the structure according to a programmed inspection sequence that controls movement of the first and second inspection devices along the structure.

3. The inspection method of claim 2, wherein the method of producing the programmed inspection sequence that controls movement of the first and second inspection devices along the structure comprises an operator commanding the second inspection device to move through data collection positions and programming the data collection positions into the programmed inspection sequence.

4. The inspection method of claim 3, wherein the structure includes substantially similar portions, and wherein during programming of the data collection positions, data collection positions for the substantially similar portions of the structure are repeated within the inspection sequence during programming.

5. The inspection method of claim 2, wherein the method of producing the programmed inspection sequence that controls movement of the first and second inspection devices along the structure comprises an operator commanding a simulated inspection device to move through data collection positions on the structure and programming the data collection positions into the programmed inspection sequence.

6. The inspection method of claim 2, wherein the programmed inspection sequence that controls movement of the first and second inspection devices along the structure is produced from surface data of the structure generated from visual surveying equipment.

7. The inspection method of claim 2, wherein the programmed inspection sequence that controls movement of the first and second inspection devices along the structure is produced from surface model data of the structure derived from CAD data.

8. The inspection method of claim 1, wherein the source inspection device and the detector inspection device are manually moved to each portion of the structure to be imaged.

9. The inspection method of claim 1, wherein the source inspection device comprises an X-ray source and the detector inspection device comprises an X-ray detector.

10. The inspection method of claim 1, wherein the source inspection device is mounted on a first gantry and the detector inspection device is mounted on a second gantry, and wherein the first and second gantries are synchronized to move in coordinated motion with each other.

11. The inspection method of claim 10, wherein the first gantry and the second gantry each comprise one or more low power actuators.

12. The inspection method of claim 1, wherein one of the first or second gantries utilizes a track assembly, and the other of the first or second gantries utilizes a rover vehicle.

13. The inspection method of claim 1, wherein the first and second inspection devices are each initialized at home positions that provide for visual contact between the first and second inspection devices.

14. The inspection method of claim 1, wherein the structure comprises an aircraft.

15. The inspection method of claim 1, wherein the particularities that the inspection method identifies comprise cracks and corrosion.

16. An inspection method for identifying particularities in a structure, the method comprising:
placing a first gantry comprising an attached first inspection device in a position located outside of the structure;
placing a second gantry comprising an attached second inspection device inside of the structure;
initializing the relative positions of the first and second inspection devices;
moving the first and second inspection devices in a coordinated manner to each of a set of data collection positions according to a programmed inspection sequence that controls movement of the first and second inspection devices along the structure; and
collecting data of the structure at each data collection position.

17. The inspection method of claim 16, wherein the first and second gantries have axes, and wherein artificial axes are utilized that allow an operator to command the first inspection device to move in its coordinate system, rather than requiring desired motion of the first inspection device to be coordinated with respect to the first gantry axes.

18. The inspection method of claim 17, wherein the artificial axes register to an aircraft coordinate system.

19. The inspection method of claim 16, wherein reverse kinematics are utilized to derive a set of second gantry motions that achieve a sequence of data collection positions for the second inspection device corresponding to a programmed sequence of data collection positions for the first inspection device.

20. The inspection method of claim 16, wherein data collection is performed when the first and second gantries are intermittently stopped.

21. The inspection method of claim 16, wherein the structure includes substantially similar portions, and wherein during programming of the data collection positions, data collection positions for the substantially similar portions of the structure are repeated within the programmed sequence of data collection positions.

22. The inspection method of claim 16, wherein one of the first or second gantries utilizes a track assembly, and the other of the first or second gantries utilizes a rover vehicle.

23. The inspection method of claim 16, wherein the structure comprises an aircraft.

24. A method for creating an inspection sequence to use in the inspection of a structure, the method comprising:
aligning an exterior gantry having an inspection device with the structure by initializing all the axes of the exterior gantry;
determining at least three reference points at locations on the structure;
determining the location and orientation of the inspection device on the exterior gantry relative to the structure via triangulation to the reference points;
determining one or more data collection positions for the inspection device on the exterior gantry;
positioning the inspection device on the exterior gantry in an orientation to the structure at a data collection position;
recording the data collection position of the inspection device on the exterior gantry;
using reverse kinematics to derive interior gantry axes motions to achieve a data collection position for an inspection device on an interior gantry corresponding to a data collection position of the inspection device on the exterior gantry; and
recording the corresponding data collection position for the inspection device on the interior gantry.

25. The method of claim 24, wherein the inspection sequence automatically moves the inspection device on the exterior gantry to a data collection position on the structure.

26. The method of claim 24, wherein the inspection device on the exterior gantry comprises an x-ray detector and the inspection device on the interior gantry comprises an x-ray source.

27. The method of claim 24, wherein the exterior and interior gantries have axes, and wherein artificial axes are utilized that allow an operator to move the inspection device on the interior gantry in its coordinate system, rather than requiring desired motion of the inspection device on the interior gantry to be coordinated with respect to interior gantry axes.

28. The method of claim 27, wherein the artificial axes register to an aircraft coordinate system.

29. The method of claim 24, wherein the exterior gantry is a master system and the interior gantry is a slave system.

30. The method of claim 24, wherein the interior gantry utilizes a track assembly and the exterior gantry utilizes a rover vehicle.

31. The method of claim 24, wherein the inspection device on the exterior gantry and the inspection device on the interior gantry are each initialized at home positions that provide for visual contact between the inspection devices.

32. The method of claim 24, wherein the structure comprises an aircraft.

33. The method of claim 24, wherein the particularities that the inspection sequence is designed to identify comprise cracks and corrosion.

34. An inspection method for identifying defects in a structure, the method comprising:
moving an exterior rover gantry having a x-ray detector inspection device to a pre-determined position outside the structure and registering the exterior rover gantry to the structure;
mounting an interior rail gantry having an x-ray source inspection device onto alignment tracks at a pre-determined position inside the structure;
aligning the x-ray detector inspection device on the exterior rover gantry with the x-ray source inspection device on the interior rail gantry;
implementing a programmed inspection sequence to automatically move the detector inspection device and the source inspection device to each of a set of image collection positions; and obtaining an x-ray image at each image collection position with the detector inspection device and the source inspection device.

35. The method of claim 34, wherein the inspection method utilizes an alignment system for aligning the x-ray detector inspection device with the x-ray source inspection device, wherein the alignment system is selected from the group of: target alignment systems, laser alignment systems, radio frequency alignment systems, physical alignment systems, and optical alignment systems.

36. The method of claim 34, wherein the exterior rover gantry is a master system and the interior rail gantry is a slave system.

37. The method of claim 34, wherein the exterior rover gantry comprises axes and the interior rail gantry comprises axes, and wherein artificial axes are utilized that allow an operator to move each of the x-ray detector inspection device and the x-ray source inspection device in its respective coordinate system, rather than requiring desired motion of the x-ray detector inspection device to be input with respect to the exterior rover gantry axes and desired motion of the x-ray source inspection device to be input with respect to the interior rail gantry.

38. The method of claim 35, wherein the artificial axes register to an aircraft coordinate system.

39. The method of claim 34, wherein reverse kinematics are utilized to derive a set of interior rail gantry motions that achieve a sequence of image collection positions for the inspection device on the interior rail gantry corresponding to a programmed sequence of image collection positions for the inspection device on the exterior rover gantry.

40. The method of claim 34, wherein the obtaining of an x-ray image at each image collection position is performed when the exterior rover gantry and the interior rail gantry are intermittently stopped.

41. The method of claim 34, wherein the inspection sequence is programmed with the set of image collection positions, and wherein the structure includes substantially similar portions, and wherein during programming of the inspection sequence, image collection positions for the substantially similar portions of the structure are repeated within the inspection sequence during programming.

42. The method of claim 34, wherein the x-ray detector inspection device and the x-ray source inspection device are each initialized at home positions that allow for physical contact between the x-ray detector inspection device and the x-ray source inspection device.

43. The method of claim 34, wherein the structure comprises an aircraft.

44. The method of claim 34, wherein the defects that the inspection method identifies comprise cracks and corrosion.

45. A system for inspecting particularities in a structure, the system comprising:
a dual gantry system, wherein an exterior gantry is configured to move externally to the structure and an interior gantry is configured to move internally to the structure;
a first inspection device mounted on the exterior gantry;
a second inspection device mounted on the interior gantry, wherein one of the first or second inspection devices comprises a detector inspection device and the other of the first or second inspection devices comprises a source inspection device; and
a gantry control system that maneuvers the detector inspection device and the source inspection device in synchronized motion with each other to each of a set of data collection positions on the structure according to a programmed inspection sequence that controls movement of the detector and source inspection devices along the structure, and wherein the detector and source inspection devices collect data at each of the set of data collection positions on the structure.

46. The system of claim 45, wherein the exterior gantry and the interior gantry each comprise one or more low power actuators.

47. The system of claim 45, further comprising a data acquisition system that controls the data collection at each of the set of data collection positions on the structure.

48. The system of claim 45, further comprising a detector touch actuator.

49. The system of claim 45, wherein the inspection system utilizes an alignment system from the group of: target alignment systems, laser alignment systems, radio frequency alignment systems, physical alignment systems, and optical alignment systems.

50. The system of claim 45, wherein the exterior gantry is a master system and the interior gantry is a slave system.

51. The system of claim 45, wherein the interior gantry comprises axes, and wherein artificial axes are utilized that allow an operator to command the second inspection device to move in its coordinate system, rather than requiring desired motion of the second inspection device to be commanded with respect to the interior gantry axes.

52. The system of claim 51, wherein the artificial axes register to an aircraft coordinate system.

53. The system of claim 45, wherein reverse kinematics are utilized to derive a set of interior gantry axes motions to effect a sequence of data collection positions for the second inspection device on the interior gantry corresponding to a programmed sequence of data collection positions for the first inspection device on the exterior gantry.

54. The system of claim 45, wherein the set of data collection positions comprise a set of image collection positions.

55. The system of claim 45, wherein the structure comprises an aircraft.

56. The system of claim 45, wherein the particularities that the inspection system identifies comprise cracks and corrosion.

* * * * *